(12) United States Patent
Pala et al.

(10) Patent No.: US 9,752,980 B1
(45) Date of Patent: Sep. 5, 2017

(54) PORTABLE CORTISOL SENSING PLATFORM BASED ON COMPACT UV LIGHT SOURCES

(71) Applicants: Nezih Pala, Miami, FL (US); Raju Sinha, Miami, FL (US); Phani Kiran Vabbina, Miami, FL (US)

(72) Inventors: Nezih Pala, Miami, FL (US); Raju Sinha, Miami, FL (US); Phani Kiran Vabbina, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/370,257

(22) Filed: Dec. 6, 2016

(51) Int. Cl.
*G01N 21/00* (2006.01)
*G01N 21/33* (2006.01)
*G01N 33/487* (2006.01)
*G01N 21/03* (2006.01)

(52) U.S. Cl.
CPC ............. *G01N 21/33* (2013.01); *G01N 21/03* (2013.01); *G01N 33/487* (2013.01); *G01N 2201/12746* (2013.01)

(58) Field of Classification Search
CPC ....... G01N 21/33; G01N 21/03; G01N 33/487
USPC ................................. 356/432–444
See application file for complete search history.

(56) References Cited

U.S. PATENT DOCUMENTS

2012/0236306 A1* 9/2012 Ostermeyer ........... G01N 21/03 356/364
2013/0252319 A1* 9/2013 Jung .................... G01N 27/021 435/287.2
2017/0055499 A1* 3/2017 Peppou ................ A01K 29/005

OTHER PUBLICATIONS

Kloet et al., "Stress and the brain: from adaptation to disease," Nature Reviews Neuroscience, Jun. 2005, pp. 463-475, vol. 6, Nature Publishing Group.
Gatti et al., "Cortisol assays and diagnostic laboratory procedures in human biological fluids," Clinical Biochemistry, Aug. 2009, pp. 1205-1217, vol. 42.
Edwards et al., "Changes in cortisol metabolism following rifampicin therapy," The Lancet, Sep. 7, 1974, pp. 549-551, vol. 304.
McEwen, "Cortisol, Cushing's Syndrome, and a shrinking brain-new evidence for reversibility," The Journal of Clinical Endocrinology & Metabolism, May 2002, pp. 1947-1948, vol. 87, No. 5.
Klopfenstein et al., "Determination of cortisol production rates with contemporary liquid chromatography-mass spectrometry to measure cortisol-d3 dilution after infusion of deuterated tracer," Clinical Biochemistry, Apr. 2011, pp. 1-12, vol. 44.
Shi et al., "Determination of cortisol in human blood sera by a new Ag(III) complex-luminol chemiluminescent system," Analytical Biochemistry, Apr. 2009, pp. 178-183, vol. 387.
Lewis et al., "An enzyme-linked immunosorbent assay (ELISA) for plasma cortisol," Journal of Steroid Biochemistry, May 1985, pp. 673-676, vol. 22, No. 5.

(Continued)

*Primary Examiner* — Tri T Ton
(74) *Attorney, Agent, or Firm* — Saliwanchik, Lloyd & Eisenschenk (57) ABSTRACT

Systems and methods for detecting a biological analyte are provided. The biological analyte can be, for example, cortisol. Detection can be achieved without external labels/mediators. Microfluidic systems can be incorporated into the optical sensor for enhanced point-of-care applications. The sensor can be used in a variety of low-power electronics for wearable applications.

10 Claims, 4 Drawing Sheets

(56) References Cited

OTHER PUBLICATIONS

Shankaran et al., "Recent advancements in surface plasmon resonance immunosensors for detection of small molecules of biomedical, food and environmental interest," Sensors and Actuators B: Chemical, Jan. 2007, pp. 158-177, vol. 121.

Kaushik et al., "Recent advances in cortisol sensing technologies for point-of-care application," Biosensors & Bioelectronics, Mar. 2014, pp. 499-512, vol. 53.

Vabbina et al., "Electrochemical cortisol immunosensors based on sonochemically synthesized zinc oxide 1D nanorods and 2D nanoflakes," Biosensors and Bioelectronics, Jan. 2015, pp. 124-130, vol. 63.

Vabbina et al., "Zinc oxide nanostructures for electrochemical cortisol biosensing," Proceedings of SPIE—The International Society for Optical Engineering, May 2014, pp. 91070U1-91070U8, vol. 9107.

https://www.sigmaaldrich.com/content/dam/sigma-aldrich/docs/Sigma/Datasheet/3/h5885-015k8804dat.pdf.

Jones et al., "Photolysis of testosterone, progesterone and 17β-estradiol by UVA light," Proceedings in AWRA Summer Specialty Conference, Jun. 25-27, 2007, pp. 1-6, Vail, Colorado.

Teir et al., "Comparison studies of the interactions between testosterone and progesterone with human serum albumin 'HSA': UV/fluorescence absorption," International Journal of Recent Scientific Research, Jul. 2015, pp. 5243-5248, vol. 6, No. 7.

Dobson et al., "What is stress, and how does it affect reproduction," Animal Reproduction Science, Jul. 2000, pp. 143-752, vol. 60.

Chen et al., "Application of nanofiber-packed SPE for determination of salivary-free cortisol using fluorescence precolumn derivatization and HPLC detection," Journal of Separation Science, Aug. 2010, pp. 2369-2375, vol. 33.

Gao et al., "HPLC-FLU detection of cortisol distribution in human hair," Clinical Biochemistry, May 2010, pp. 677-682, vol. 43.

Appel et al., "A fluorimetric assay for cortisol," Analytical and Bioanalytical Chemistry, Sep. 2005, pp. 182-186, vol. 383.

Manenschijn et al., "Evaluation of a method to measure long term cortisol levels," Steroids, Sep. 2011, pp. 1032-1036, vol. 76.

Shimada et al., "Determination of salivary cortisol by ELISA and its application to the assessment of the Circadian rhythm in children," Hormone Research, Jun. 1995, pp. 213-217, vol. 44. No. 5.

Atashbar et al., "QCM biosensor with ultra thin polymer film," Sensors and Actuators B: Chemical, Jun. 2005, pp. 945-951, vol. 107.

Attili et al., "A piezoelectric immunosensor for the detection of cortisol," Analytical Letters, Jun. 1995, pp. 2149-2159, vol. 28, No. 12.

Mitchell et al., "Rapid ultrasensitive measurement of salivary cortisol using nano-linker chemistry coupled with surface plasmon resonance detection," Analyst, 2009, pp. 380-386, vol. 134.

* cited by examiner

PORTABLE CORTISOL SENSING PLATFORM BASED ON COMPACT UV LIGHT SOURCES

BACKGROUND

Psychological stress is associated with increased risk of several health conditions including cardiovascular disease, autoimmune disorders, infectious disease, and mental illnesses (B. S. McEwen, Stress, adaptation, and disease. Allostasis and allostatic load, Ann. N. Y. Acad. Sci. 840 (1998) 33-44). The link between psychological stress and physical ailments can be observed in the biological responses associated with stress, namely the production of cortisol, a major glucocorticoid in humans.

Cortisol is synthesized and secreted by the zona fasciculata and the zona reticularis of the adrenal cortex for the purpose of facilitating the human body to adapt to changing environmental conditions (H. Dobson, and R. F. Smith, "What is stress, and how does it affect reproduction?," Animal reproduction science, vol. 60, pp. 743-752, 2000). In its free form, cortisol plays an important role in the regulation of, for example, blood pressure, glucose levels, carbohydrate metabolism, and homeostasis of the cardiovascular, immune, renal, and endocrine systems (E. R. De Kloet, M. Joëls, and F. Holsboer, "Stress and the brain: from adaptation to disease," Nature Reviews Neuroscience, vol. 6, pp. 463-475, 2005.; R. Gatti, G. Antonelli, M. Prearo, P. Spinella, E. Cappellin, and F. Elio, "Cortisol assays and diagnostic laboratory procedures in human biological fluids," Clinical biochemistry, vol. 42, pp. 1205-1217, 2009; R. Fraser, M. C. Ingram, N. H. Anderson, C. Morrison, E. Davies, J. M. C. Connell, Cortisol Effects on Body Mass, Blood Pressure, and Cholesterol in the General Population, Hypertension, 33, 1364-1368, 1999; D. S. Charney, Psychobiological Mechanism of Resilience and Vulnerability: Implications for Successful Adaptation to Extreme Stress, Am. J. Psychiatry, 161, pp. 195-216, 2004).

Any abnormality in cortisol levels inhibits inflammation, depresses the immune system, and increases fatty and amino acid levels in blood. Persistent increment of cortisol may affect brain functions leading to aging of the brain. A decrease in cortisol levels contributes to the development of Addison's disease having symptoms such as weight loss, fatigue, and darkening of skin folds and scars, while elevated cortisol levels can lead to Cushing's disease with the symptoms of obesity, fatigue, and bone fragility (O. M. Edwards, J. M. Galley, R. J. Courtenay-Evans, J. Hunter, and A. D. Tait, "Changes in cortisol metabolism following rifampicin therapy," The Lancet, vol. 304, pp. 549-551, 1974; B. S. McEwen, "Cortisol, Cushing's syndrome, and a shrinking brain—new evidence for reversibility," The Journal of Clinical Endocrinology & Metabolism, vol. 87, pp. 1947-1948, 2002). Cortisol levels can increase by ten-fold following surgery or other major trauma, as the steroid acts to prevent vascular collapse, reduce inflammation, and suppress immune response. Chronically elevated cortisol is associated with the neuroendocrine causal pathway linking environmental or psychological distress to poor health outcomes (M. van Eck, H. Berkhof, N. Nicolson, J. Sulon, The effects of perceived stress, traits, mood states, and stressful daily events on salivary cortisol, Psychosom. Med., 58, pp. 447-58). Hence, cortisol is considered a major stress hormone and is, therefore, an effective biomarker for stress.

Existing cortisol detection techniques are generally limited to the conventional laboratory-based techniques such as chromatography (B. J. Klopfenstein, J. Q. Purnell, D. D. Brandon, L. M. Isabelle, and A. E. DeBarber, "Determination of cortisol production rates with contemporary liquid chromatography—mass spectrometry to measure cortisol-d3 dilution after infusion of deuterated tracer," Clinical Biochemistry, 44, pp. 430-434, 2011; L. Q. Chen, X. J. Kang, J. Sun, J. J. Deng, Z. Z. Gu, and Z. H. Lu, "Application of nanofiber—packed SPE for determination of salivary—free cortisol using fluorescence precolumn derivatization and HPLC detection," Journal of separation science, 33, pp. 2369-2375, 2010; W. Gao, Q. Xie, J. Jin, T. Qiao, H. Wang, L. Chen, H. Deng, and Z. Lu, "HPLC-FLU detection of cortisol distribution in human hair," Clinical biochemistry, vol. 43, pp. 677-682, May 2010), radioimmunoassay (MA) (D. Appel, R. D. Schmid, C. A. Dragan, M. Bureik, and V. B. Urlacher, "A fluorimetric assay for cortisol," Analytical and bioanalytical chemistry, 383, pp. 182-186, 2005), electrochemiluminescence immunoassay (ECLIA) (H. Shi, X. Xu, Y. Ding, S. Liu, L. Li, and W. Kang, "Determination of cortisol in human blood sera by a new Ag (III) complex-luminol chemiluminescent system," Analytical biochemistry, 387, pp. 178-183, 2009), enzyme-linked immunosorbent assay (ELISA) (J. G. Lewis, and P. A. Elder, "An enzyme-linked immunosorbent assay (ELISA) for plasma cortisol," Journal of steroid biochemistry, 22, pp. 673-676, 1985; L. Manenschijn, J. W. Koper, S. W. J. Lamberts, and E. F. C. van Rossum, "Evaluation of a method to measure long term cortisol levels," Steroids, 76, pp. 1032-1036, 2011; M. Shimada, K. Takahashi, T. Ohkawa, M. Segawa, and M. Higurashi, "Determination of salivary cortisol by ELISA and its application to the assessment of the circadian rhythm in children," Hormone Research in Paediatrics, 44, pp. 213-217, 1995), surface plasmon resonance (SPR) (J. S. Mitchell, T. E. Lowe, and J. R. Ingram, "Rapid ultrasensitive measurement of salivary cortisol using nano-linker chemistry coupled with surface plasmon resonance detection," Analyst, 134, pp. 380-386, 2008; D. R. Shankaran, K. V. Gobi, and N. Miura, "Recent advancements in surface plasmon resonance immunosensors for detection of small molecules of biomedical, food and environmental interest," Sensors and Actuators B: Chemical, 121, pp. 158-177, 2007), quartz crystal microbalance (QCM) (M. Z. Atashbar, B. Bejcek, A. Vijh, and S. Singamaneni, "QCM biosensor with ultra thin polymer film," Sensors and Actuators B: Chemical, 107, pp. 945-951, 2005), and piezoelectric immunosensor (B. S. Attili, and A. A. Suleiman, "A piezoelectric immunosensor for the detection of cortisol," Polymer—Plastics Technology and Engineering, 28, pp. 2149-2159, 1995). These laboratory techniques are not only expensive, laborious, and time-consuming, but also often require complex systems, assay formation complexity, large sample volume, and time-consuming incubation and separation procedures, which altogether limit them being adapted in point-of-care (POC) applications. Although several electrochemical immuno-sensing platforms have been developed recently for POC cortisol detection, they often require complex synthesis and fabrication steps involving the immobilizing matrix of high surface functionality, high biomolecule loading, and small resistance to electron transport (A. Kaushik, A. Vasudev, S. K. Arya, S. K. Pasha, and S. Bhansali, "Recent advances in cortisol sensing technologies for point-of-care application," Biosensors and Bioelectronics, 53, pp. 499-512, 2014; P. K. Vabbina, A. Kaushik, N. Pokhrel, S. Bhansali, and N. Pala, "Electrochemical cortisol immunosensors based on sono-chemically synthesized zinc oxide 1D nanorods and 2D nanoflakes," Biosensors and Bioelectronics, 63, pp. 124-130, 2015; P. K. Vabbina, A. Kaushik, K. Tracy, S. Bhansali, and N. Pala, "Zinc oxide nanostructures for electrochemical cortisol biosensing," Proc. SPIE, 9107, pp. 91070U-91070U, 2014).

Additionally, a major limitation of currently available cortisol immunoassay kits and immunosensors is their cross-reactivity and interference with other cortisol structural analogs such as, for example, progesterone and prednisolone (S. Tunn, G. Pappert, P. Willnow, M. Krieg, Multicentre evaluation of an enzyme-immunoassay for cortisol determination., Clin. Chem. Clin. Biochem., 28, pp. 929-35, 1990; I. A. Ionita, D. M. Fast, F. Akhlaghi, Development of a sensitive and selective method for the quantitative analysis of cortisol, cortisone, prednisolone and prednisone in human plasma., J. Chromatogr. B. Analyt. Technol. Biomed. Life Sci., 877, pp. 765-72, 2009).

BRIEF SUMMARY

Due to the aforementioned limitations of related art cortisol sensing technology, developing a simple, label-free, high sensitivity, high selectivity, and cost-effective sensing device is desired for implementing personalized health monitoring and diagnosis with point-of-care (POC) cortisol detection applications.

Embodiments of the subject invention provide materials and methods for fabricating and using an optical sensor system for detecting biological analytes. Advantageously, detection can be achieved without external labels/mediators. In some embodiments, microfluidic systems can be incorporated into the optical sensor for enhanced POC applications. In other embodiments, the optical sensor system can be integrated with an appropriate specimen holder and peripheral electronics to be used with mobile electronic devices such as, for example, smartphones and tablets. Further, technologies provided herein can be used in a variety of low-power electronics for wearable applications.

In one embodiment, an apparatus can be used for measuring the concentration of a target analyte in a test sample. In some embodiments, the apparatus comprises a light source, a photodetector, a device capable of measuring and displaying a response (e.g., voltage or current output) of the photodetector, and an optically transparent sample container for holding the test sample. In some embodiments, the sample container can comprise an absorbent material including, but not limited to, paper, fabric, and polymers. The photodetector can be positioned opposite the light source, and the sample container can be positioned between the light source and the photodetector.

In another embodiment, a method for measuring concentration of a target analyte in a test sample can utilize an apparatus as described herein. In some embodiments, the method comprises, as an initial step, establishing a calibration curve at a particular wavelength of incident light emitted by the light source of the sensing apparatus.

In yet another embodiment, a sensing device can comprise an apparatus as described herein packaged in a casing configured to facilitate wearable applications for measuring concentration of a target analyte in a test sample, which is collected on or near the sweat glands of a human subject. In some embodiments, the sensing device is placed in direct contact with human skin.

BRIEF DESCRIPTION OF THE DRAWINGS

FIG. 2B shows an image of an experimental setup with an LED and a photodetector placed face-to-face on a breadboard.

DETAILED DESCRIPTION

Embodiments of the subject invention provide materials and methods for fabricating and using an optical sensor for detecting biological analytes. Advantageously, detection can be achieved without external labels/mediators. In some embodiments, microfluidic systems can be incorporated into the optical sensor for enhanced point-of-care applications. Further, technologies provided herein can be used in variety of low-power electronics for wearable applications.

Figures 2A, 2C:
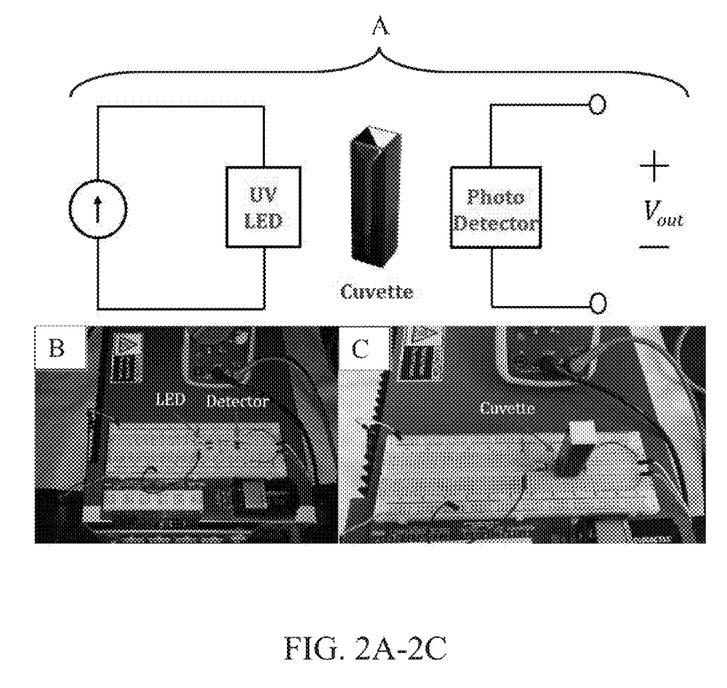
FIG. 2A shows a schematic circuit representation of an ultraviolet (UV) light emitting diode (LED) optical sensor according to an embodiment of the subject invention.
FIG. 2C shows an image of a complete setup of an embodiment of the optical sensor system with a cuvette placed in between the LED and the photodetector.

In one embodiment, an apparatus for measuring the concentration of a target analyte in a test sample can comprise a light source, a photodetector, a device capable of measuring and displaying output of the photodetector, and a storage unit for holding the test sample. In some embodiments, the storage unit can be positioned between the light source and the photodetector such that the photodetector can measure the absorption of the emitted light by the test sample (FIGS. 2A-2C). In a particular embodiment, the storage unit is an optically transparent cuvette.

The sensing apparatuses described herein are capable of identifying and measuring concentration of biological target analytes because various biomolecules possess different optical properties when subjected to an incident light of a given wavelength. Biomolecules capable of absorbing light give off a distinct absorption peak, resulting in a signature spectrum that can be used to distinguish such biomolecules. In some embodiments, the target analyte is a steroid hormone selected from cortisol, progesterone, prednisolone, testosterone, and estradiol.

Figure 1:
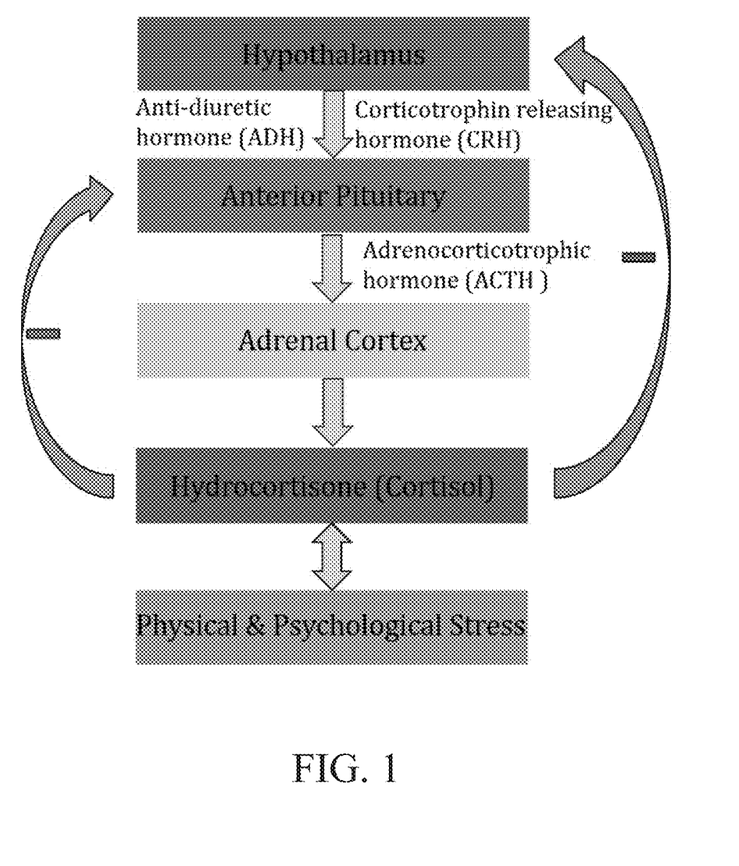
FIG. 1 shows the production of cortisol regulated by the hypothalamic-pituitary-adrenal system under the influence of physical and psychological stress.

In some embodiments, the sensing apparatus detects the presence, and evaluates the concentration, of cortisol, a steroid hormone also known as hydrocortisone whose secretion is regulated by the hypothalamic-pituitary-adrenal system (FIG. 1). Cortisol has a broadband absorption range of between about 220 nm and about 260 nm in the UV spectrum, with the peak absorption present at approximately 240 nm (https://www.sigmaaldrich.com/content/dam/sigma-aldrich/docs/Sigma/Datasheet/3/h5885-015k8804dat.pdf).

In some embodiments, the apparatus measures the optical absorption of a test sample at various wavelengths chosen within the broadband absorption range specific to the target analyte of interest. Optical absorption is measured as the absolute numeric difference between the response of the photodetector of a blank sample, e.g., an empty portion of a cuvette holding a sample, and the response of the sample held in the cuvette. In some embodiments, an empty cuvette can be used as a blank sample. At a given wavelength of incident light, the concentration of the target analyte present in a sample is positively correlated with the optical absorption of the same sample measured using the apparatus provided herein.

In some embodiments, the photodetector is a semiconductor photodiode capable of converting light into electronic signals such as, for example, voltage or current. Non-limiting examples of photodetectors include silicon-based, germanium-based, and GaAs-based photodiodes. Those skilled in the art would recognize that other semiconductor-based photodiodes now known or hereafter developed can also be used for detecting the optical absorption of a target analyte in a sample. In an exemplary embodiment, a multimeter is employed to measure and display the response of the photodetector in the measurement apparatus.

Depending upon the value of the peak absorption of a target analyte, the wavelength of the light source provided herein can be adjusted accordingly. In specific embodiments, for the detection of cortisol, the light source can be an ultraviolet (UV) light emitting diode (LED) or a laser diode (LD) configured to emit, or capable of emitting, light with a wavelength within the absorption range of cortisol, which is between about 220 nm and about 260 nm. The wavelength of the incident light can be the same as or near the peak absorption of a target analyte.

In another embodiment, a method for measuring concentration of a target analyte in a test sample can utilize a measurement apparatus as described herein.

In order to determine the concentration of a target analyte in an unknown test sample, it is necessary to establish a quantitative correlation between analyte concentration and optical absorption. In some embodiments, a method comprises, as an initial step, establishing a calibration curve at a particular wavelength of incident light emitted by the light source of the sensing (measurement) apparatus. In an embodiment, the establishment of a calibration curve requires the optical absorption of a sufficient number of calibration samples with distinctly different concentrations of the target analyte of interest to be measured using a measurement apparatus as described herein. In a particular embodiment, the establishment of a calibration curve requires the optical absorption of at least three calibration samples.

In some embodiments, the wavelength of light from which the largest optical sensitivity is derived is the optimal wavelength to be employed for the light source. The optical sensitivity is the slope of the linear correlation between the optical absorption and the analyte concentration of the calibration samples.

Figure 4:
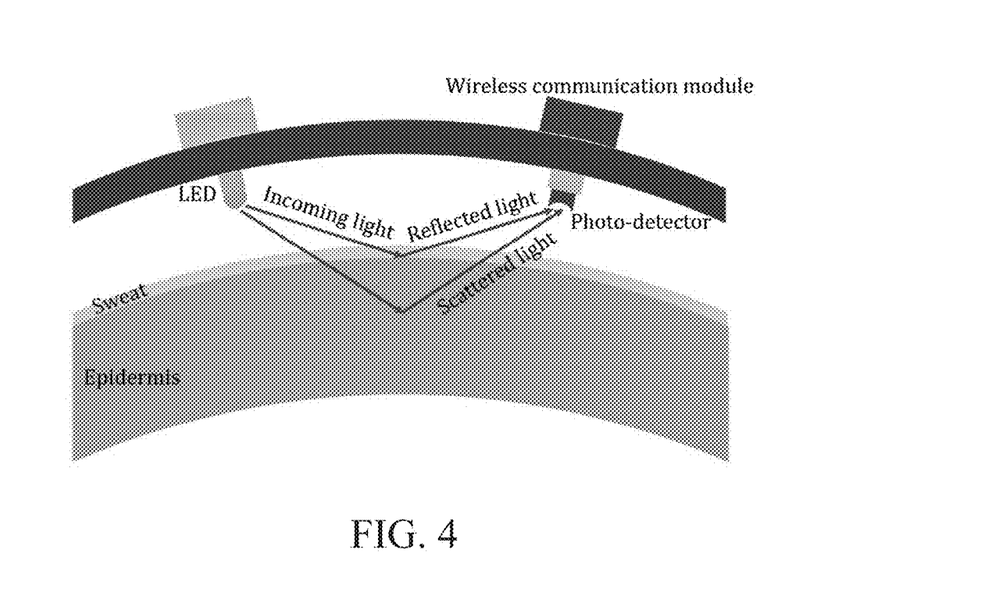
FIG. 4 is a schematic view of a wearable cortisol optical sensor according to an embodiment of the subject invention.

In yet another embodiment, a sensing apparatus as described herein can be packaged into a device configured to facilitate wearable applications for measuring concentration of a target analyte, e.g., cortisol, in a test sample, which is collected on or near the sweat glands of the skin of a human subject (FIG. 4). In some embodiments, the sensing device is placed in direct contact with human skin. Advantageously, the device provided herein can be integrated with additional electronics and/or microfluidic systems for screening of analytes in point-of-care (POC) applications.

Figure 5:
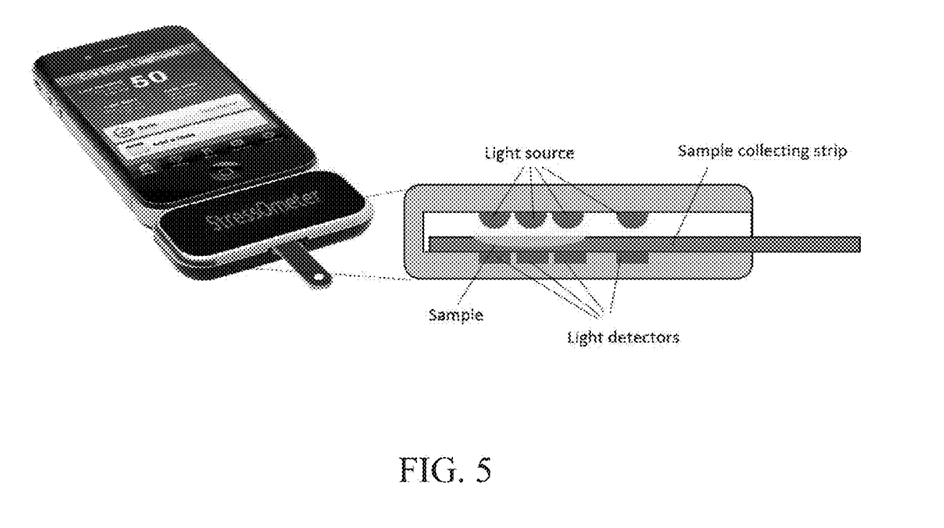
FIG. 5 shows a schematic of an optical cortisol sensor system integrated with a mobile device and a cross-sectional view of the sensor system.

In a particular embodiment, the sensing device, when equipped with an appropriate sample holder (e.g., a sample-collecting strip as shown in FIG. 5) and peripheral electronics, can be integrated with mobile electronic devices such as, for example, smartphones and tablets (see, for example, FIG. 5).

In some embodiments, the test sample is a product of human transdermal diffusion process, which is generated by the apocrine and/or eccrine sweat glands. Some embodiments provide that the test sample is secreted from human skin perspiration. While both types of sweat glands are located in the dermis region, the eccrine sweat gland, being near the epidermis layer, releases sweat directly to the skin surface through pores, allowing a test sample to be placed in contact with the device.

In an embodiment, perspiration triggered by stress can be captured and evaluated for cortisol concentration by the wearable device, because cortisol is an effective biomarker for physical and psychological stress. Alternatively, using a different incident light wavelength, stress level can also be evaluated based on a decrease in concentration of one or more of other steroid hormones such as, for example, testosterone, progesterone, prednisolone, and/or estradiol.

In some embodiments, the target analyte is a steroid hormone selected from cortisol, progesterone, prednisolone, testosterone, and estradiol. In a particular embodiment, the target analyte is cortisol. Advantageously, the device can selectively detect cortisol in the presence of other steroid hormones.

In some embodiments, the device comprises a wireless communication module capable of analyzing the output of the photodetector and numerically computing the concentration of the target analyte.

In some embodiments, a portion of the light generated by the light source (e.g., a UV LED or a UV LD), is reflected from the epidermis of the skin, while the rest penetrates approximately 40 μm into the epidermis layer and is scattered back. The scattered and reflected light is then collected by the photodetector. The subsequent data analysis can be carried out by a wireless communication module connected to the photodetector.

In further embodiments, the integrated sensing device comprises multiple electronic platforms for receiving user input and displaying the analyte concentration. In some embodiments, the measured analyte concentration can be shown via a display capable of portraying data in the form of visual text and/or images. Non-limiting examples of the display include devices comprising liquid crystal materials, electrophoretic material, and/or electrochromic materials that are commonly found in applications such as electronic paper, computer monitors, handheld devices and the like.

In an embodiment, a sensing device as described herein can be integrated with additional components for various low-power wearable applications. Examples of an integrated device include, but are not limited to, wrist watches, bracelets, and arm bands; apparel such as shirts, jackets, and pants; accessories such as gloves, glasses, goggles, necklaces, and lanyards; headsets and headbands; and shoes.

In some embodiments, wearable devices can incorporate aesthetic designs such that the analyte concentration can be monitored in a human subject without the need for the subject to wear bulky electronic systems.

In some embodiments, a sensing device can be incorporated (e.g., retrofitted) into devices manufactured by third parties.

Embodiments of the integrated devices comprise a protective casing that helps prevent or inhibit circuitry damage and hold the device components together. The materials that can be used to develop the casings include, but are not limited to, polymers, fabrics, and metals.

POC testing is particularly desirable for today's healthcare needs because it rapidly delivers results to medical practitioners and enables faster consultation. Early diagnosis allows a practitioner to begin treatment sooner, thus avoiding deterioration of a patient's condition. Advantageously, many embodiments of the device as described herein integrated with additional electronic components and/or microfluidic systems can enable POC testing of biological target analytes such as, for example, stress biomarker cortisol, without requiring elaborate laboratory testing equipment and apparatuses.

Other objects, features, and advantages of the invention will be apparent to those skilled in the art from the detailed description of the invention which will now follow, taken in conjunction with the tables, drawings, and the accompanying claims.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

EXAMPLES

The following are examples for illustrative purposes and should not be construed as limiting.

Commercially available UV LEDS, UVTOP240, UVTOP250 and UVTOP260 LEDs purchased from Sensor Electronic Technology, Inc. were used in developing the optical sensor.

These LEDs were hermetically sealed in metal-glass transistor outline (TO) packages with peak emission wavelengths at 240 nm, 250 nm and 260 nm, respectively. Maximum-rated value of DC forward current in those LEDs is 25 mA. KEITHLEY 2400 sourcemeter was used directly to drive the LEDs with 20 mA of constant current with a compliance of 6.2V-13V. A Silicon (Si) photodiode (S1226-44BQ) was used as the photodetector with a quantum efficiency of 75% and photo sensitivity of greater than 0.1 A/W at 240 nm wavelength.

Experiments described herein were set up in a circuit breadboard. The LED and the photodetector were placed face-to-face in the board leaving about 15 mm space in between. A quartz cuvette with 10 mm path length and 400 µL volume capacity holding a test sample was placed in between the LED and detector. A FLUKE 115 multimeter was used to record the voltage at the two terminals of the detector. FIGS. 2A-2C depict the experimental setup in details.

Example 1—Detection of Cortisol Concentration with UV LED Sensor (I)

A sample solution containing different concentrations of cortisol was prepared by dissolving appropriate amount of hydrocortisone in 10 ml methanol solvent. 0.108 mg, 0.199 mg, 0.3 mg, 0.4 mg, 0.5 mg, 0.6 mg, and 0.725 mg of hydrocortisone was respectively dissolved in 10 mL of methanol to prepare seven different cortisol solutions having concentration of 30 µM, 55 µM, 83 µM, 110 µM, 138 µM, 166 µM and 200 µM, respectively. The solutions were subsequently stored at 4° C. A Finnpipette was used to take 200 µL of solution each time to fill the cuvette.

In order to avoid any error introduced by displacement of the cuvette paced between the LED and the photodetector for each set of measurements, the output voltage reading was first taken with a blank cuvette placed between the LED and the photodetector as a reference. The cuvette was then filled with a cortisol solution of interest and the output was measured again. The absolute potential difference between the reference and the second reading quantifies the amount of absorbed UV by the corresponding cortisol solution. By utilizing the 260-nm LED and placing the blank cuvette in between the LED and photodetector facing the transparent sides towards them, the output was taken by the photodetector measuring 392 mV of potential. Then, without changing the position of the cuvette, the cuvette was filled with 200 µL of 30 µM cortisol solution and the output was measured to be 389 mV. The absolute difference between these two readings ($\Delta V$), which was 3 mV, quantified the amount of absorbed UV by the cortisol solution having a concentration of 30 µM.

Figure 3:
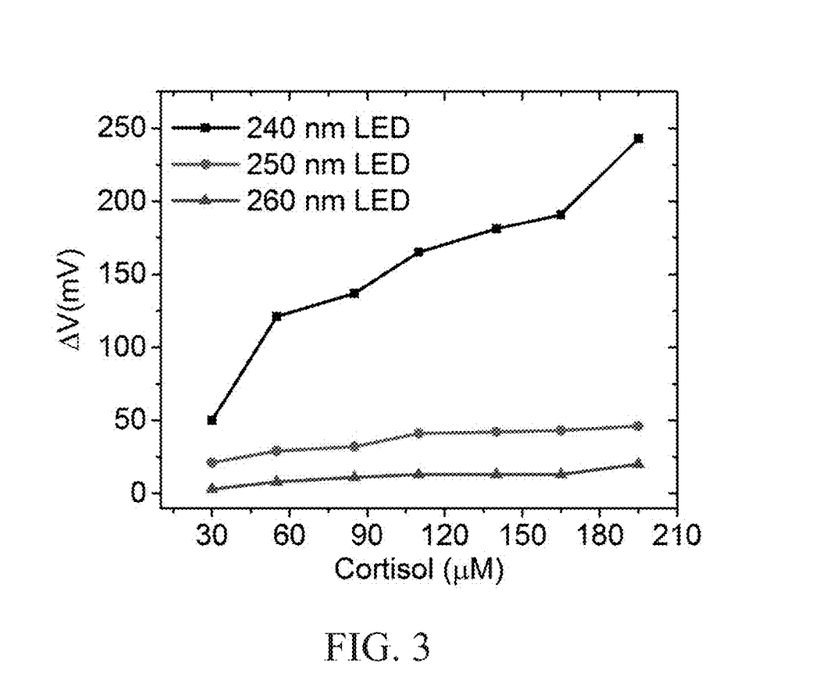
FIG. 3 shows a plot of photo-response at the photodetector as a function of cortisol concentration when analyzed with different UV LED wavelengths.

Similarly, the output of other solutions having different concentrations of cortisol was measured by changing the solution in the cuvette. After each measurement, the cuvette was rinsed with deionized (DI) water and dried it nitrogen ($N_2$) to make sure there was no solution left from the previous measurement. The potential difference measured with the 260-nm light source was plotted against each cortisol concentration in FIG. 3 (triangular data points). It is evident that the potential difference in output varied linearly with increasing cortisol concentration and reached a maximum of 20 mV for the 200 µM cortisol solution, implying that the maximum absorption of UV occurred at that concentration. By using linear curve fitting, the slope of the curve was calculated to obtain the detection sensitivity of the sensor, which was 0.08 mV/µM at 260 nm of wavelength.

Example 2—Detection of Cortisol Concentration with UV LED Sensor (II)

Similar measurements were taken by the apparatus and methods provided herein by utilizing a 250-nm LED source. The results are plotted in circular data points in FIG. 3. The plot suggests that the difference in potential output is larger at each concentration than what was observed by using the 260 nm LED, though the general trend of the data remained the same (i.e., difference in potential output increased with increasing concentration of cortisol). The data confirmed that higher absorption occurred at 250 nm wavelength than at 260 nm. Specifically, it was found that the difference in potential output to be 21 mV and 46 mV for solutions with 30 µM and 200 µM of cortisol, respectively, and the detection sensitivity was determined to be 0.15 mV/µM.

Example 3—Detection of Cortisol Concentration with UV LED Sensor (III)

A third set of measurements was taken with the use of a 240-nm LED, whose illumination produced the maximum absorption peak of cortisol in the UV spectrum (https://www.sigmaaldrich.com/content/dam/sigma-aldrich/docs/Sigma/Datasheet/3/h5885-015k8804dat.pdf). The results are shown in rectangular data points in FIG. 3. It was observed that the difference in potential output had the same increasing trend with an increase in cortisol concentration as the results obtained from the previously used LEDs. However, the 240-nm LED produced the largest response (with a maximum sensitivity of 1 mV/µM) at each cortisol concentration than both the 250-nm and 260-nm LEDs.

Example 4—Detection Sensitivity

Selectivity is an essential parameter for sensing devices. Cortisol, progesterone, testosterone, and estradiol are three common steroid hormones found in human saliva and sweat. These steroid hormones produce absorption peaks at different positions in UV spectra. Estradiol has an absorption peak at around 200 nm, which is distinct and far away from other steroids' absorption peaks (J. M. Jones, T. Borch, R. B. Young, J. G. Davis, and C. R. Simpson, "Photolysis of testosterone, progesterone and 17β-estradiol by UVA light," Proc. In AWRA summer specialty conference, Vail, Colo., 25-27, 2007). Cortisol, progesterone, and testosterone show absorption peak at 240 nm, 244 nm, and 245 nm, respectively (J. M. Jones, T. Borch, R. B. Young, J. G. Davis, and C. R. Simpson, "Photolysis of testosterone, progesterone and 17β-estradiol by UVA light," Proc. In AWRA summer specialty conference, Vail, Colo., 25-27, 2007). In order to increase the detection selectivity of the UV LED based cortisol sensor, human serum albumin (HSA) can be added to each test sample, which can shift the absorption peaks of progesterone and testosterone to about 280 nm, leaving the cortisol at its original peak of 240 nm, easily differentiating cortisol from other hormones using the same light source (M. M. A. Teir, H. Alsamamra, and S. Darwish, "Comparison studies of the interactions between testosterone and progesterone with human serum albumin "HSA": UV/fluorescence absorption," International Journal of Recent Scientific Research, 6, pp. 5243-5248, 2015).

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

[1] E. R. De Kloet, M. Joëls, and F. Holsboer, "Stress and the brain: from adaptation to disease," Nature Reviews Neuroscience, vol. 6, pp. 463-475, June 2005.

[2] R. Gatti, G. Antonelli, M. Prearo, P. Spinella, E. Cappellin, and F. Elio, "Cortisol assays and diagnostic laboratory procedures in human biological fluids," Clinical biochemistry, vol. 42, pp. 1205-1217, August 2009.

[3] H. Dobson, and R. F. Smith, "What is stress, and how does it affect reproduction?," Animal reproduction science, vol. 60, pp. 743-752, July 2000.

[4] O. M. Edwards, J. M. Galley, R. J. Courtenay-Evans, J. Hunter, and A. D. Tait, "Changes in cortisol metabolism following rifampicin therapy," The Lancet, vol. 304, pp. 549-551, September 1974.

[5] B. S. McEwen, "Cortisol, Cushing's syndrome, and a shrinking brain—new evidence for reversibility," The Journal of Clinical Endocrinology & Metabolism, vol. 87, pp. 1947-1948, March 2002.

[6] B. J. Klopfenstein, J. Q. Purnell, D. D. Brandon, L. M. Isabelle, and A. E. DeBarber, "Determination of cortisol production rates with contemporary liquid chromatography—mass spectrometry to measure cortisol-d3 dilution after infusion of deuterated tracer," Clinical Biochemistry, vol. 44, pp. 430-434, April 2011.

[7] L. Q. Chen, X. J. Kang, J. Sun, J. J. Deng, Z. Z. Gu, and Z. H. Lu, "Application of nanofiber—packed SPE for determination of salivary—free cortisol using fluorescence precolumn derivatization and HPLC detection," Journal of separation science, vol. 33, pp. 2369-2375, August 2010.

[8] W. Gao, Q. Xie, J. Jin, T. Qiao, H. Wang, L. Chen, H. Deng, and Z. Lu, "HPLC-FLU detection of cortisol distribution in human hair," Clinical biochemistry, vol. 43, pp. 677-682, May 2010.

[9] D. Appel, R. D. Schmid, C. A. Dragan, M. Bureik, and V. B. Urlacher, "A fluorimetric assay for cortisol," Analytical and bioanalytical chemistry, vol. 383, pp. 182-186, September 2005.

[10] H. Shi, X. Xu, Y. Ding, S. Liu, L. Li, and W. Kang, "Determination of cortisol in human blood sera by a new Ag (III) complex-luminol chemiluminescent system," Analytical biochemistry, vol. 387, pp. 178-183, April 2009.

[11] J. G. Lewis, and P. A. Elder, "An enzyme-linked immunosorbent assay (ELISA) for plasma cortisol," Journal of steroid biochemistry, vol. 22, pp. 673-676, May 1985.

[12] L. Manenschijn, J. W. Koper, S. W. J. Lamberts, and E. F. C. van Rossum, "Evaluation of a method to measure long term cortisol levels," Steroids, vol. 76, pp. 1032-1036, September 2011.

[13] M. Shimada, K. Takahashi, T. Ohkawa, M. Segawa, and M. Higurashi, "Determination of salivary cortisol by ELISA and its application to the assessment of the circadian rhythm in children," Hormone Research in Paediatrics, vol. 44, pp. 213-217, June 1995.

[14] J. S. Mitchell, T. E. Lowe, and J. R. Ingram, "Rapid ultrasensitive measurement of salivary cortisol using nano-linker chemistry coupled with surface plasmon resonance detection," Analyst, vol. 134, pp. 380-386, November 2008.

[15] D. R. Shankaran, K. V. Gobi, and N. Miura, "Recent advancements in surface plasmon resonance immunosensors for detection of small molecules of biomedical, food and environmental interest," Sensors and Actuators B: Chemical, vol. 121, pp. 158-177, January 2007.

[16] M. Z. Atashbar, B. Bejcek, A. Vijh, and S. Singamaneni, "QCM biosensor with ultra thin polymer film," Sensors and Actuators B: Chemical, vol. 107, pp. 945-951, June 2005.

[17] B. S. Attili, and A. A. Suleiman, "A piezoelectric immunosensor for the detection of cortisol," Polymer—Plastics Technology and Engineering, vol. 28, pp. 2149-2159, June 1995.

[18] A. Kaushik, A. Vasudev, S. K. Arya, S. K. Pasha, and S. Bhansali, "Recent advances in cortisol sensing technologies for point-of-care application," Biosensors and Bioelectronics, vol. 53, pp. 499-512, March 2014.

[19] P. K. Vabbina, A. Kaushik, N. Pokhrel, S. Bhansali, and N. Pala, "Electrochemical cortisol immunosensors based on sonochemically synthesized zinc oxide 1D nanorods and 2D nanoflakes," Biosensors and Bioelectronics, vol. 63, pp. 124-130, January 2015.

[20] P. K. Vabbina, A. Kaushik, K. Tracy, S. Bhansali, and N. Pala, "Zinc oxide nanostructures for electrochemical cortisol biosensing," Proc. SPIE, vol 9107, pp. 91070U-91070U, May 2014.

[21] https://www.sigmaaldrich.com/content/dam/sigma-aldrich/docs/Sigma/Datasheet/3/h5885-015k8804dat.pdf

[22] J. M. Jones, T. Borch, R. B. Young, J. G. Davis, and C. R. Simpson, "Photolysis of testosterone, progesterone and 17β-estradiol by UVA light," Proc. In AWRA summer specialty conference, Vail, Colo., Jun. 25-27, 2007.

[23] M. M. A. Teir, H. Alsamamra, and S. Darwish, "Comparison studies of the interactions between testosterone and progesterone with human serum albumin "HSA":

UV/fluorescence absorption," International Journal of Recent Scientific Research, vol. 6, pp. 5243-5248, July 2015.

What is claimed is:

1. A sensing device for measuring the concentration of cortisol in a test sample, the sensing device comprising:
   a UV light source configured to emit light of a wavelength between 220 nm and 260 nm;
   a semiconductor photodiode configured to measure optical absorption of the test sample in terms of a response of the photodiode;
   a wireless communication module configured to analyze the response of the photodiode and compute the concentration of a target analyte; and
   a casing enclosing the UV light source and the semiconductor photodiode, the casing being adapted to facilitate wearable applications,
   the photodiode and the light source being positioned such that the photodiode receives a signal reflected and scattered by the test sample,
   the device being configured to match an electrical potential corresponding to the measured optical absorption to the concentration of cortisol and selectively detect cortisol when one or more steroid hormones selected from progesterone, prednisolone, testosterone, and estradiol are present, and
   the device being configured to shift an absorption peak of at least one of progesterone, prednisolone, testosterone, and estradiol.

2. The device according to claim 1, further comprising a platform for receiving user input and a display module for outputting the concentration of cortisol in the test sample.

3. The device according to claim 1, wherein the test sample is a human physiological fluid selected from sweat and saliva.

4. The device according to claim 1, wherein the device is configured to be placed on the skin of a human subject.

5. The device according to claim 1, wherein the device is configured to measure the concentration of cortisol without the use of any external label or mediator.

6. The device according to claim 1, further comprising a microfluidic system incorporated therein.

7. A sensing apparatus for measuring concentration of a target analyte in a test sample, the sensing apparatus comprising:
   a light source comprising at least one UV LED;
   a semiconductor photodetector;
   a device configured to measure and display a response of the photodetector; and
   an optically transparent sample container for holding the test sample,
   the photodetector being positioned opposite the light source and the sample container being positioned between the light source and the photodetector,
   the device being configured to match an electrical potential measured by the photodetector to the concentration of the target analyte, and
   the device being configured to shift an absorption peak of at least one hormone in the test sample.

8. The apparatus according to claim 7, wherein the target analyte is a steroid hormone selected from cortisol, progesterone, prednisolone, testosterone, and estradiol,
   wherein the test sample is a human physiological fluid selected from sweat, saliva, blood, plasma, serum, urine, cerebrospinal fluid, and tears,
   wherein the optically transparent sample container for holding the test sample is a quartz cuvette, and
   wherein the light source emits light at a specific wavelength determined by the optical absorption peak of the target analyte.

9. The apparatus according to claim 7, wherein the apparatus is configured to measure the concentration of cortisol without the use of any external label or mediator.

10. The apparatus according to claim 7, further comprising a microfluidic system incorporated therein.

\* \* \* \* \*